United States Patent
Anderson et al.

(10) Patent No.: US 10,687,800 B2
(45) Date of Patent: Jun. 23, 2020

(54) SUTURING DEVICE HAVING STABILIZING MECHANISM

(71) Applicant: Dura Tap LLC, Wayne, PA (US)

(72) Inventors: David Greg Anderson, Villanova, PA (US); Mark F. Kurd, Wayne, PA (US); Jay Tapper, Wayne, PA (US); Jens Johnson, Austin, TX (US)

(73) Assignee: DURASTAT LLC, Wayne, PA (US)

( * ) Notice: Subject to any disclaimer, the term of this patent is extended or adjusted under 35 U.S.C. 154(b) by 271 days.

(21) Appl. No.: 15/842,007

(22) Filed: Dec. 14, 2017

(65) Prior Publication Data

US 2019/0183483 A1    Jun. 20, 2019

(51) Int. Cl.
| | |
|---|---|
| *A61B 17/12* | (2006.01) |
| *A61B 17/04* | (2006.01) |
| *A61B 17/06* | (2006.01) |
| *A61B 17/00* | (2006.01) |
| *A61B 17/02* | (2006.01) |

(52) U.S. Cl.
CPC .......... *A61B 17/0469* (2013.01); *A61B 17/06* (2013.01); *A61B 17/06066* (2013.01); *A61B 17/0057* (2013.01); *A61B 17/0218* (2013.01); *A61B 17/0482* (2013.01); *A61B 2017/00336* (2013.01); *A61B 2017/00477* (2013.01); *A61B 2017/0608* (2013.01); *A61B 2017/06095* (2013.01)

(58) Field of Classification Search
CPC ..... A61B 17/04; A61B 17/06; A61B 17/0469; A61B 17/0057; A61B 17/0482; A61B 17/0483

See application file for complete search history.

(56) References Cited

U.S. PATENT DOCUMENTS

| | | |
|---|---|---|
| 2,906,124 A | 9/1959 | Chaney |
| 5,518,211 A | 5/1996 | Gaskill et al. |
| 6,190,312 B1 | 2/2001 | Fowler, Jr. |
| 2002/0022764 A1 | 2/2002 | Smith et al. |
| 2002/0156422 A1* | 10/2002 | Takagi .............. A61M 25/0631 604/164.12 |
| 2004/0073090 A1 | 4/2004 | Butler et al. |

(Continued)

FOREIGN PATENT DOCUMENTS

WO    2017136022    8/2017

OTHER PUBLICATIONS

International Search Report filed in PCT/US2018/064648 dated Feb. 27, 2019.

*Primary Examiner* — Vi X Nguyen
(74) *Attorney, Agent, or Firm* — Rankin, Hill & Clark LLP

(57) ABSTRACT

A suturing device includes an elongate body, an actuator, a needle holder and a stabilizer. The elongate body includes a proximal end portion and a distal end portion. The actuator interacts with the elongate body and is operable between a first operating position and a second operating position. The needle holder extends away from the distal end portion or is provided as part of the distal end portion of the elongate body. The needle holder defines a needle passage and a distal opening. The stabilizer connects with the elongate body and is configured to engage an upper edge of an associated tubular retractor so as to limit movement of the elongate body with respect to the associated tubular retractor when the stabilizer is engaged with the tubular retractor.

14 Claims, 8 Drawing Sheets

(56) References Cited

U.S. PATENT DOCUMENTS

| | | |
|---|---|---|
| 2007/0156245 A1* | 7/2007 | Cauthen, III ...... A61B 17/0057 623/17.16 |
| 2007/0282272 A1 | 12/2007 | Bannon |
| 2012/0265019 A1 | 10/2012 | Garcia-Bengochea |
| 2017/0156547 A1 | 6/2017 | Neumann |

* cited by examiner

SUTURING DEVICE HAVING STABILIZING MECHANISM

BACKGROUND

The present disclosure relates generally to surgery and the placement of sutures, and more particularly, to devices and methods for the suture repair of tissue.

Surgical closure techniques using sutures is one approach to tissue repair. In some instances, however, these techniques can be difficult to execute due to anatomic constraints, obstruction of visualization by blood or other bodily fluids, and the proximity to nerve rootlets. In some instances, these challenges can be further complicated when using minimally invasive techniques such as, for example, a tubular retractor. Traditional tools and devices can be limited and, in some instances, lack maneuverability to avoid obstructions and/or to enable adequate passage of the needle and suture through the tissue.

SUMMARY

A suturing device includes an elongate body, an actuator, a needle holder and a stabilizer. The elongate body includes a proximal end portion and a distal end portion. The actuator interacts with the elongate body and is operable between a first operating position and a second operating position. The needle holder extends away from the distal end portion or is provided as part of the distal end portion of the elongate body. The needle holder defines a needle passage and a distal opening. The stabilizer connects with the elongate body and is configured to engage an upper edge of an associated tubular retractor so as to limit movement of the elongate body with respect to the associated tubular retractor when the stabilizer is engaged with the tubular retractor.

DETAILED DESCRIPTION

Figure 1:
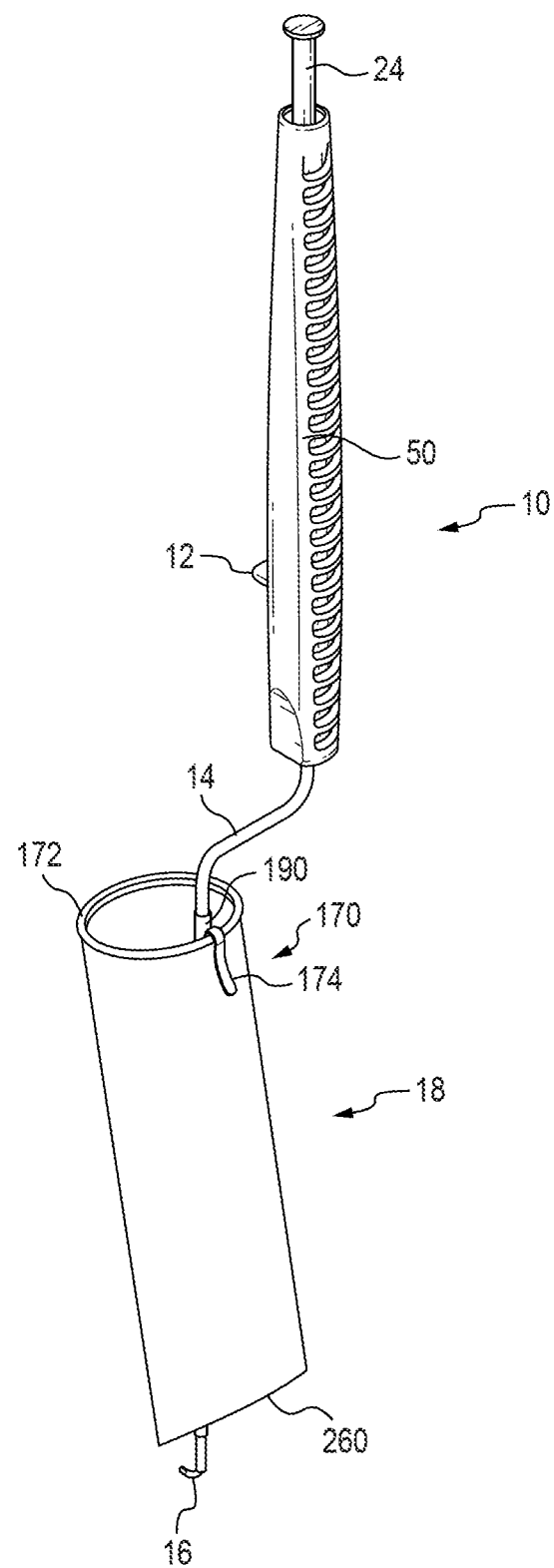
FIG. 1 is a perspective view of a suturing device having a stabilizer and received within a tubular retractor.
Figure 3:
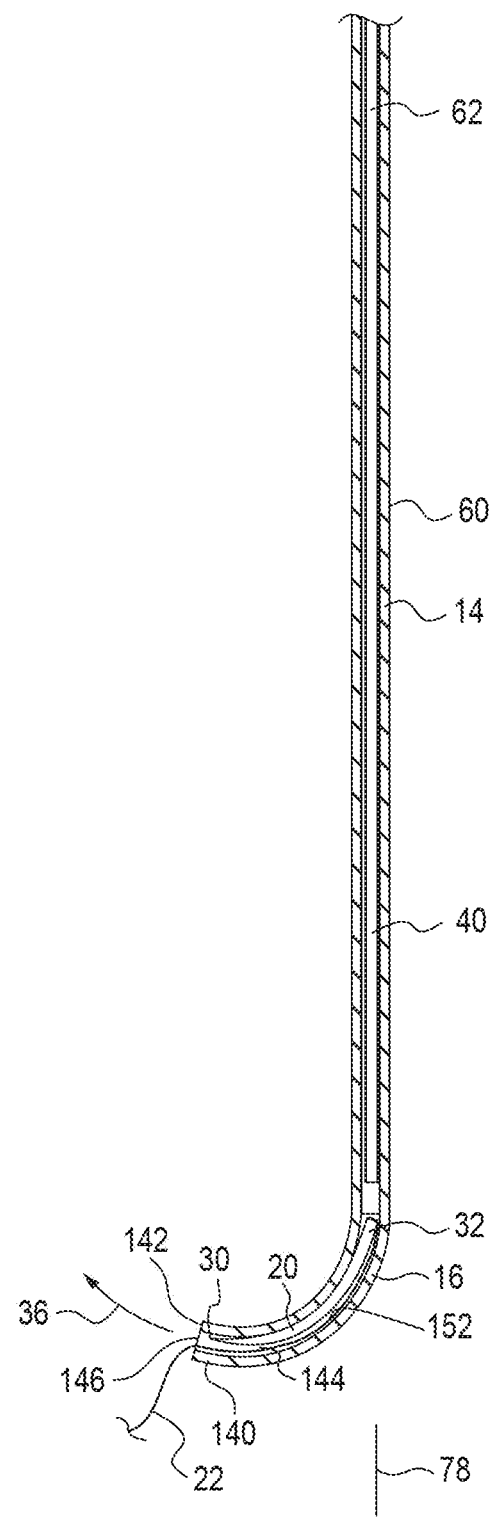
FIG. 3 is a cross-sectional view of a distal portion of the suturing device of FIG. 1.

FIG. 1 depicts an example of a suturing device 10 that is useful to suture tears in tissue and that can be used in many different types of surgical procedures. The suturing device 10 generally includes an actuator having a button 12, an elongate body 14, and a needle holder 16. The suturing device 10 is particularly useful during a minimally invasive surgical procedure that is performed through a tubular retractor 18 or other small surgical portal to accurately locate a needle 20 and a suture 22, which are shown in FIG. 3, to facilitate passing the needle 20 through target tissue to be sutured.

The needle 20 in the illustrated embodiment is a curved needle having a first end 30, which is pointed, and a second end 32, which is opposite to the first end. The needle 20 can be similar to commercially available curved needles made from known materials. The needle 20 could also be formed from a malleable, or flexible, material such that the needle 20 could follow a curve when positioned within the needle holder 16, which can be curved, and then later straighten after exiting the needle holder 16. Both the needle holder 16 and the needle 20 can take other configurations.

The actuator, which includes the button 12 and a plunger 24, is more particularly described in U.S. application Ser. No. 15/654,878, which is incorporated by reference herein. Actuation of the actuator moves the needle 20 in an advance direction 36 with respect to the needle holder 16. The needle 20 moves from a retracted position, which is shown in FIG. 3, to a released condition in which the needle 20 is released from the needle holder 16. When in the released condition, the surgeon can grasp the needle 20, for example with forceps, and pull the needle 20 and the suture 22. The suture 22 connects with the needle 20 and extends from the second end 32 of the needle 20. The suture 22 can be swaged to the second end 32 of the needle 20. The suture 22 can also connect with the needle 20 in other conventional manners. The suture 22 can be acquired from known suture manufacturers.

The actuator is operable between a first operating position and a second operating position. Movement of the actuator from the first operating position toward the second operating position moves the needle 20 in the advance direction 36 with respect to the needle holder 16 thus moving the needle 20 toward the released condition in which the needle 20 is released from the needle holder 16. In the illustrated embodiment, the actuator includes a flexible section, which in the illustrated embodiment is made up of a wire 40, which can be made from nitinol. The flexible section is configured to bend within the needle holder 16 when the actuator is moved from the first operating position toward the second operating position. The other components of the actuator are described in more detail in U.S. application Ser. No. 15/654, 878 and will not be described herein for the sake of brevity.

The elongate body 14 connects with a handle 50 in the illustrated embodiment. The elongate body 14 in the illustrated embodiment is in the form of a cannula. The elongate body 14 has an outer surface 60, which is smooth, and defines a track 62 that receives a portion of the actuator, more particularly the wire 40 in the illustrated embodiment. As described above, the elongate body 14 is a cannula and the track 62 is a lumen that receives the wire 40 of the actuator. The track 62 need not encircle the wire 40, but could be U-shaped. In the depicted embodiments, the elongate body 14 is circular in a cross section taken normal to the longest dimension of the elongate body 14, however, the elongate body 14 could take alternative configurations, such as polygonal or U-shaped.

The elongate body 14 has a bayonet configuration in the illustrated embodiment; however, the elongate body 14 could take alternative configurations, such as straight along a longitudinal axis. The elongate body 14 includes the proximal end portion 70 and a distal end portion 72 connected by an intermediate portion 74. The proximal end portion 70 connects with the handle 50. In the illustrated embodiment, the needle holder 16 is received in and connected with the elongate body 14 and extends away from the distal end portion 72. Alternatively, the needle holder 16 can be provided as part of the distal end portion 72 of the elongate body 14. The elongate body 14 is made from a rigid metal material; however, if desired at least a portion of the elongate body 14 may be made from a malleable or flexible material to allow the surgeon to bend at least a portion of the elongate body 14 into a desirable configuration for insertion into an animal body during a surgical procedure. In the illustrated embodiment, an outer diameter of the elongate body 14 is constant between the proximal end portion 70 and the distal end portion 72. The outer diameter can be less than 3.5 mm, which provides a very slim device to enhance the line of sight for a surgeon during the surgical procedure.

The intermediate portion 74 is positioned between the proximal end portion 70 and the distal end portion 72. The proximal end portion 70 extends along a proximal end portion longitudinal axis 76. The distal end portion 72 extends along a distal end portion longitudinal axis 78, which is offset from the proximal end portion longitudinal axis 76 in a forward direction. In the illustrated embodiment, the distal end portion longitudinal axis 78 is offset from the proximal end portion longitudinal axis 76 about 25 mm. The proximal end portion 70 transitions to the intermediate portion 74 through a proximal bend 82 and the intermediate portion 74 transitions to the distal end portion 72 through a distal bend 84. In the illustrated embodiment, the proximal bend 82 and the distal bend 84 are both angled internally 135 degrees.

The proximal end portion 70 of the elongate body 14 is received in the handle 50. The elongate body 14 and the needle holder 16 are rotatable with respect to the handle 50 about a rotational axis, which in the illustrated embodiment is coaxial with the proximal end portion longitudinal axis 76; however, rotation of the elongate body 14 and the needle holder 16 with respect to the handle 50 requires a greater amount of force to be applied on the elongate body 14 or needle holder 16 than the force that is typically applied to the elongate body 14 or the needle holder 16 while a surgeon is using the suturing device 10 during a suturing procedure.

The needle holder 16 extends away from the distal end portion 72 or is provided as part of the distal end portion 72 of the elongate body 14. With reference to FIG. 3, the needle holder 16 is a hollow tubular member. In the illustrated embodiment, a portion of the needle holder 16 that is aligned with the distal end portion longitudinal axis 78 is received inside the elongate body 14; however, the needle holder 16 could be formed as part of the elongate body, e.g., both the elongate body 14 and the needle holder 16 could be made from one tubular stock material. The needle holder 16 depicted in the illustrated embodiment is a curved needle holder that generally follows a constant radius such that the suturing device 10 can have J-hook configuration at a distal end thereof. In the illustrated embodiment, the needle holder 16 is not intended to be removable from the elongate body 14; however, in an alternative arrangement the needle holder 16 can selectively connect with the elongate body 14 via a mechanical connection such as a friction fit or a bayonet connection.

With reference to FIG. 3, the needle holder 16 includes a distal end section 140 having a distal-most tip 142. The needle holder 16 defines a needle passage 144 that is in communication with the track 62 and a distal opening 146. The distal opening 146 is offset from the distal end portion longitudinal axis 78 in a forward direction. In the embodiment depicted in FIG. 3, at least a portion of the suture 22 extends along the needle passage 144 from the second end 32 of the needle 20 toward the distal opening 146 between the needle 20 and an inner surface 152 of the needle holder 16 when the needle 20 is received in the needle passage 144 and the actuator is in the first operating position. The distal-most tip 142 is offset from the distal end portion longitudinal axis 78 in a direction perpendicular from the distal end portion longitudinal axis 78 a distance of less than 7 mm. Common tubular retractors used during minimally invasive spinal surgery procedures have diameters measuring between 14 mm to 22 mm. By spacing the distal-most tip 142 offset from the distal end portion longitudinal axis 78 less than 7 mm, the surgeon can locate the elongate body 14 along the central axis of the tubular retractor and rotate the suturing device around the central axis without contacting the side of the tubular retractor.

Figure 4:
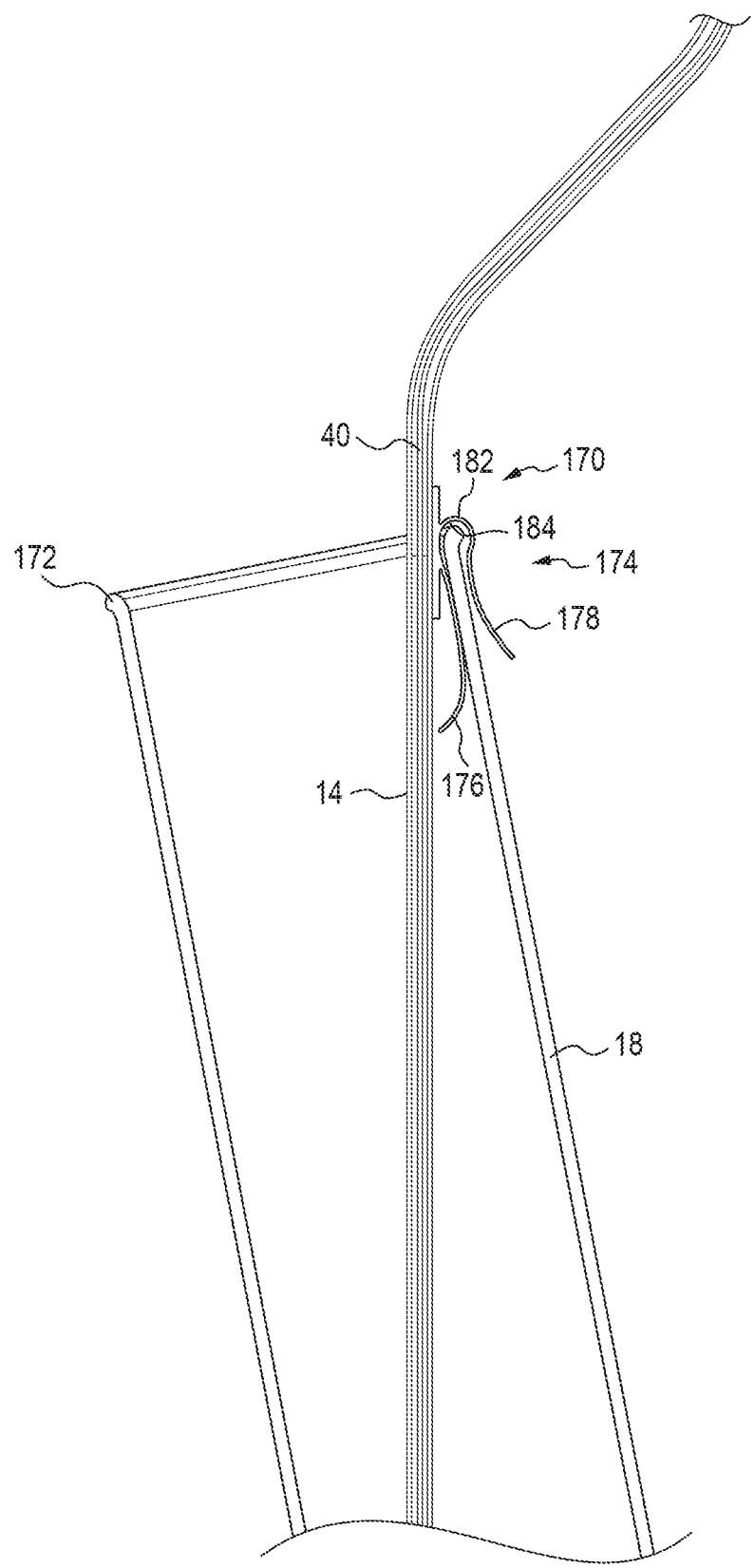
FIG. 4 is a cross-sectional view of a portion of the suturing device, stabilizer and tubular retractor depicted in FIG. 1.

The suturing device 10 includes a stabilizer 170 connected with the elongate body 14 and configured to engage an upper edge 172 of the tubular retractor 18 so as to limit movement of the elongate body 14 with respect to the tubular retractor 18 when the stabilizer is engaged with the tubular retractor 18. The tubular retractor 18 is an example of a conventional tubular retractor used in minimally invasive surgical procedures, and it can take different configurations, such as including a handle. In the embodiment depicted in FIGS. 1-4, the stabilizer 170 includes a metal formed spring clip 174 (hereinafter referred to as a first metal formed spring clip) configured to engage the upper edge 172 of the tubular retractor 18. With reference to FIG. 4, the first metal formed spring clip 174 includes a curved inner leg 176, a curved outer leg 178 and a substantially upside-down U-shaped apex portion 182 joining the curved inner leg 176 to the curved outer leg 178. The curved inner leg 176 is configured to be received within the tubular retractor 18 and the curved outer leg 178 is positioned outside of the tubular retractor 18 when the stabilizer 170 is engaged with the tubular retractor 18. The curved inner leg 176 is spaced from the curved outer leg 178 a minimum distance, which is less than or no more than 25% greater than a maximum wall thickness of the upper edge 172 of the tubular retractor 18, which can be a conventional 14-22 mm tubular retractor.

In a more general sense and with reference to FIG. 4, the stabilizer 170 includes a tubular retractor contact surface 184 extending away from the elongate body 14 configured to engage the upper edge 172 of the tubular retractor 18. In this embodiment, the tubular retractor contact surface 184 is an inner surface of the first metal formed spring clip 174, and the inner surface can be provided on at least one of the curved inner leg 176, the curved outer leg 178 and the apex portion 182.

With reference back to FIG. 1, the stabilizer 170 includes a second metal formed spring clip 190 connected with the first metal formed spring clip 174 and engaged with the elongate body 14. The first metal formed spring clip 174 connects with the second metal formed spring clip 190 via a weld. Alternatively, the first metal formed spring clip 174 can connect with the second metal formed spring clip 190 in other conventional manners, and could also connect with the second metal formed spring clip 190 by being unitarily formed with the second metal formed spring clip 190, e.g., the first metal formed spring clip 174 and the second metal formed spring clip 190 could be formed from a single piece of metal. Also, even though they are referred to a metal formed spring clips 174 and 190, the spring clips 174 and 190 can be made from other materials, e.g., resilient plastic.

The second metal formed spring clip 190 can be C-shaped in a cross section taken normal to the distal end portion longitudinal axis 78. Both the first metal formed spring clip 174 and the second metal formed spring clip 190 can be made from a resilient metal. The second metal formed spring clip 190 can clip onto the elongate body 14 and the first metal formed spring clip 174 can clip onto the upper edge 172 of the tubular retractor 18. The second metal formed spring clip 190 connects with the elongate body 14 and is slidable along the elongate body 14 (e.g., parallel with the distal end portion longitudinal axis 78) when connected with the elongate body 14. When the stabilizer 170 is engaged (e.g., in contact with or clipped onto) the upper edge 172 of the tubular retractor 18, movement of the elongate body 14 with respect to the tubular retractor 18 is inhibited, which can be useful when suturing.

Figure 5:
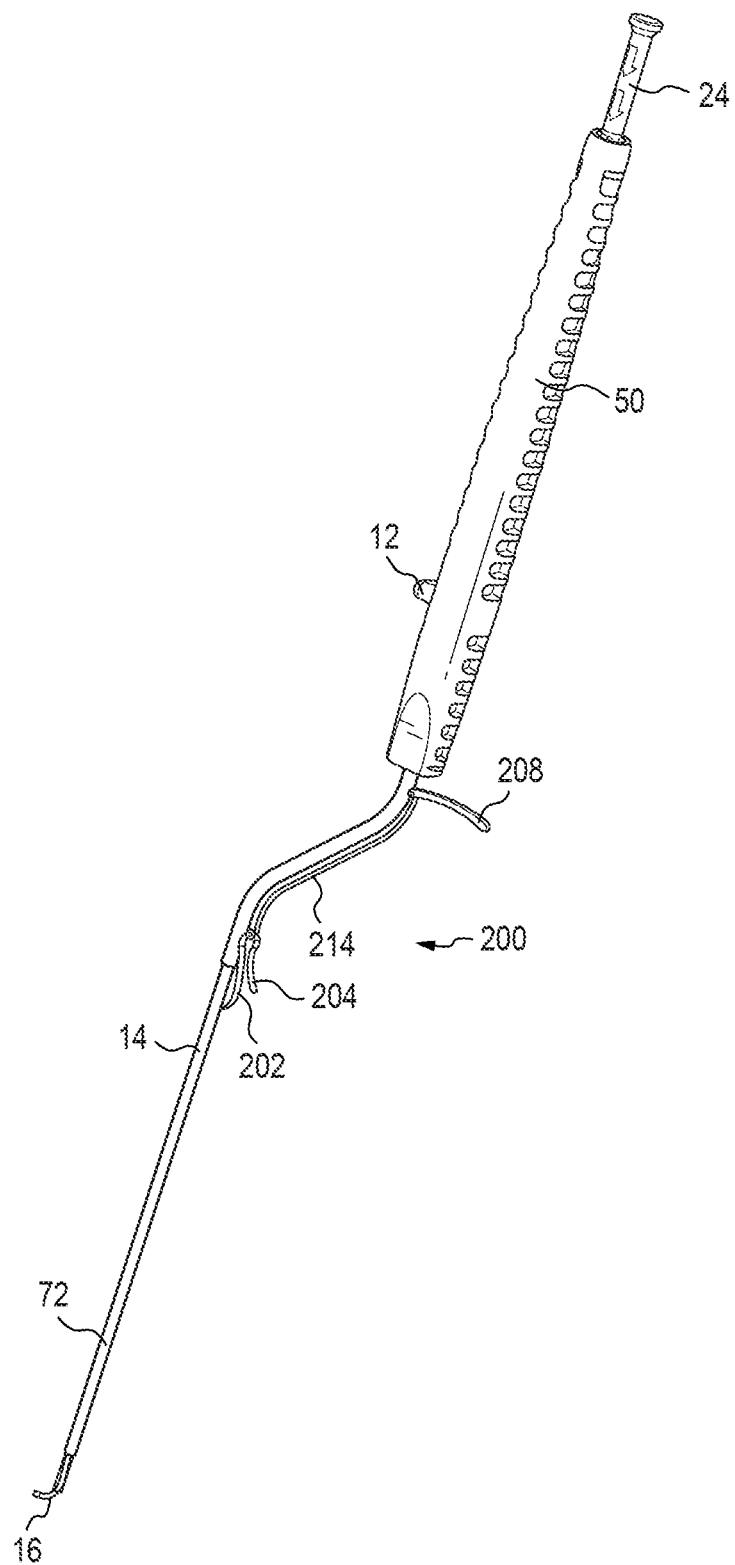
FIG. 5 is a perspective view of a suturing device having an alternative stabilizer.

FIG. 5 depicts an alternative stabilizer 200 connected with the elongate body 14 and configured to engage the upper edge 172 (FIGS. 1 and 2) of the tubular retractor 18 so as to limit movement of the elongate body 14 with respect to the tubular retractor 18 when the stabilizer 200 is engaged with the tubular retractor 18. The stabilizer 200 includes an inner leg 202 configured to be received within the tubular retractor 18 (FIGS. 1 and 2) and an outer leg 204 connected with the inner leg 202. The outer leg 204 is positioned outside of the tubular retractor 18 when the stabilizer 200 is engaged with the tubular retractor 18.

Figure 6:
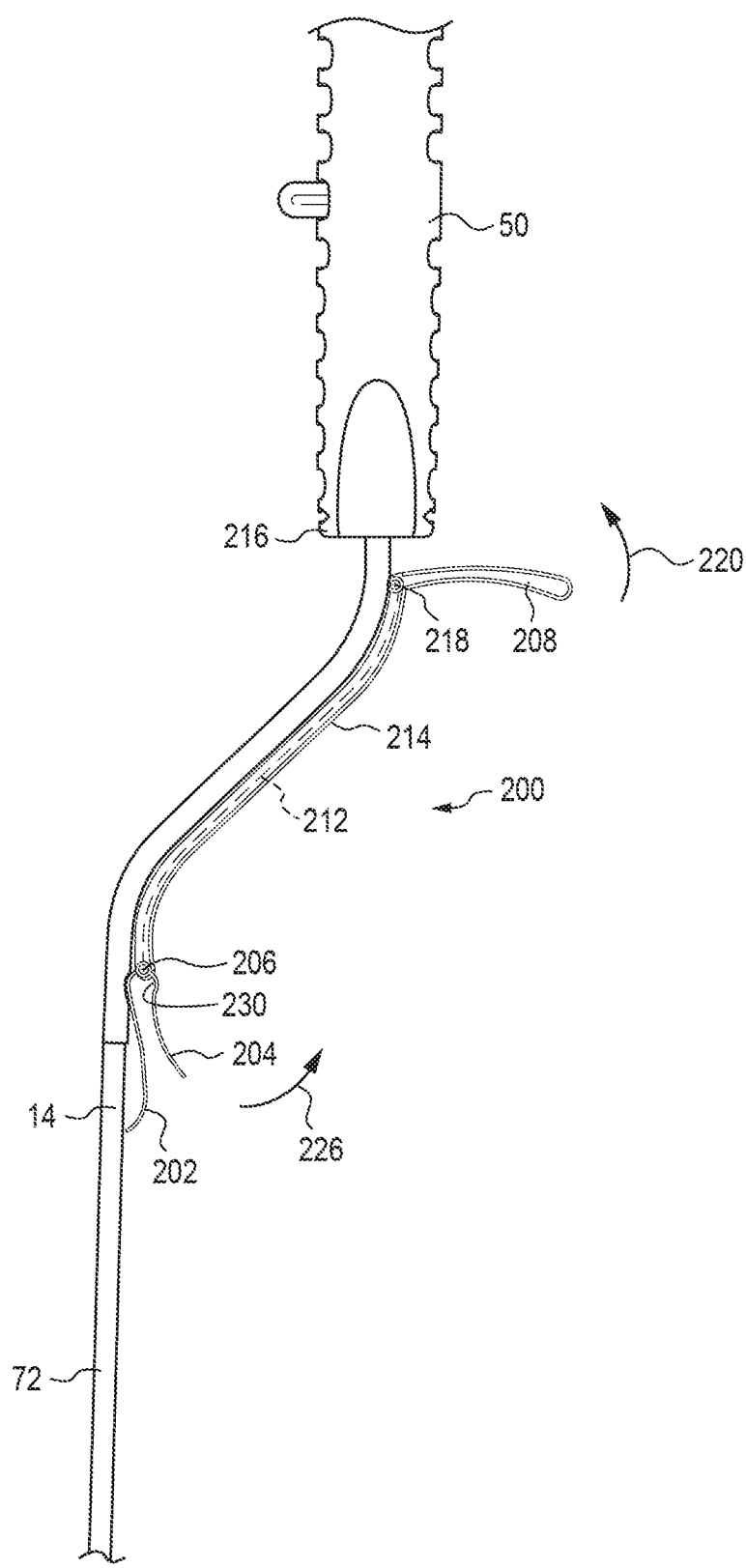
FIG. 6 is a side view of a portion of the suturing device depicted in FIG. 5.
Figure 7:
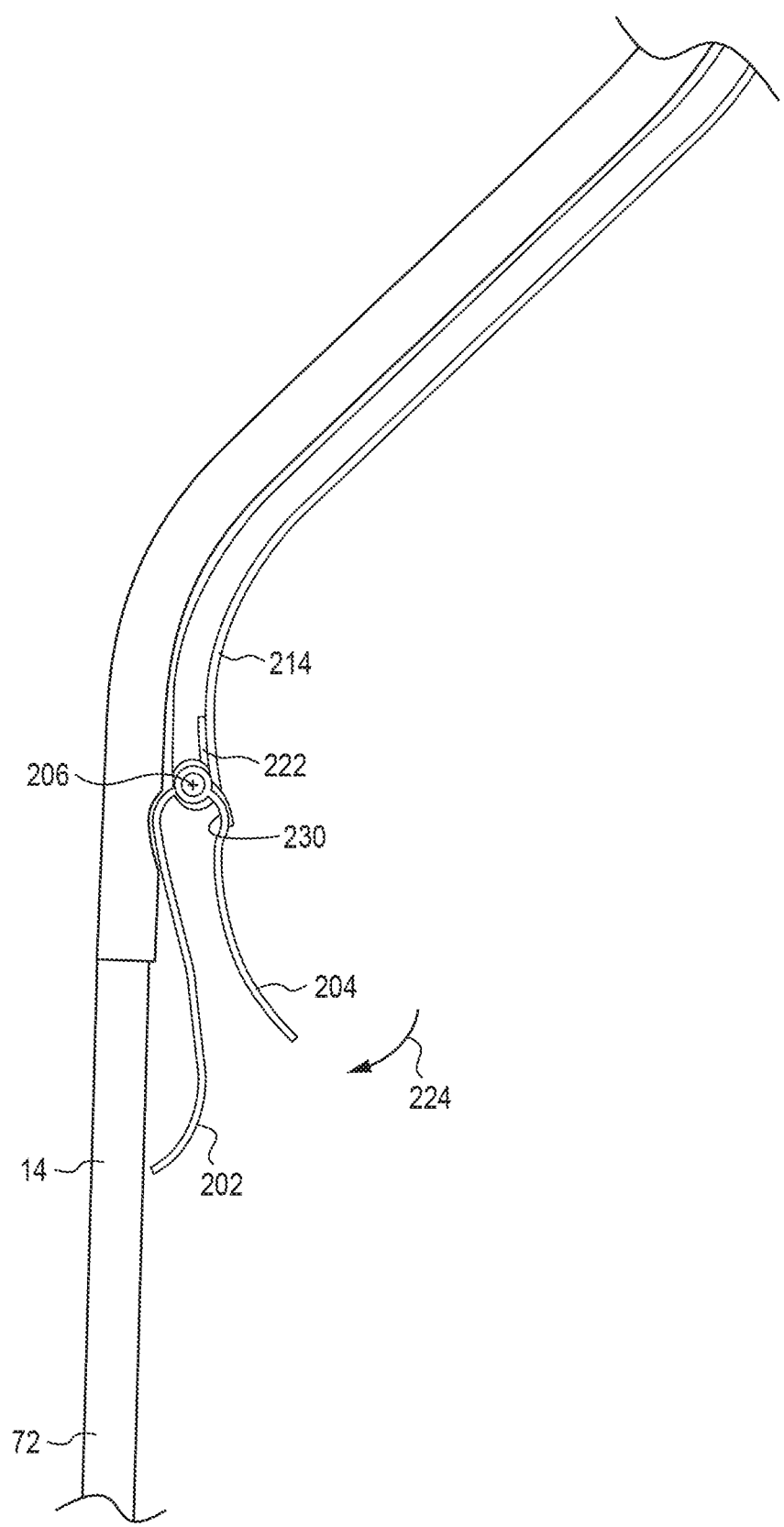
FIG. 7 is a cross-sectional view of a portion of the suturing device depicted in FIG. 5.

In the embodiment depicted in FIGS. 5-7, the outer leg 204 is movable, and more particularly, pivotable about a pivot axis 206, with respect to the inner leg 202. A trigger 208 operatively connects with the outer leg 204 via a cable, pulley or other transmission, which is schematically depicted as a transmission system 212 located within a housing 214 in FIG. 6, such that movement of the trigger 208 results in movement of the outer leg 204 with respect to the inner leg 202. The housing 214 connects with and is fixed to for movement with the elongate body 14. The outer leg 204 pivotally connects with the housing 214.

The trigger 208 is located adjacent to a distal end 216 of the handle 50 so as to be easily operated by the surgeon. In the illustrated embodiment, the trigger 208 is spaced from the distal end 216 of the handle 50 in a distal direction, i.e., toward the distal-most tip 142 (FIG. 3). The trigger 208 is configured to be movable from a first position (shown in FIG. 6) toward a second position, for example, in which the trigger 208 is rotated about a trigger pivot axis 218 in the direction of arrow 220. The trigger 208 pivotally connects with the housing 214.

The outer leg 204 can be biased toward the inner leg 202. In the illustrated embodiment and as more clearly seen in FIG. 7, a coil spring 222 contacts the housing 214 and the outer leg 204 and biases the outer leg 204 to pivot in the direction of arrow 224 about the pivot axis 206 toward the inner leg 202. Pivotal movement of the trigger 208 in the direction of arrow 220 (FIG. 6) from the first position toward the second position overcomes the biasing force biasing the outer leg 204 toward the inner leg 202 to move (e.g., pivot) the outer leg 204 with respect to the inner leg 202 in the direction of the arrow 226 (FIG. 6).

Figure 2:
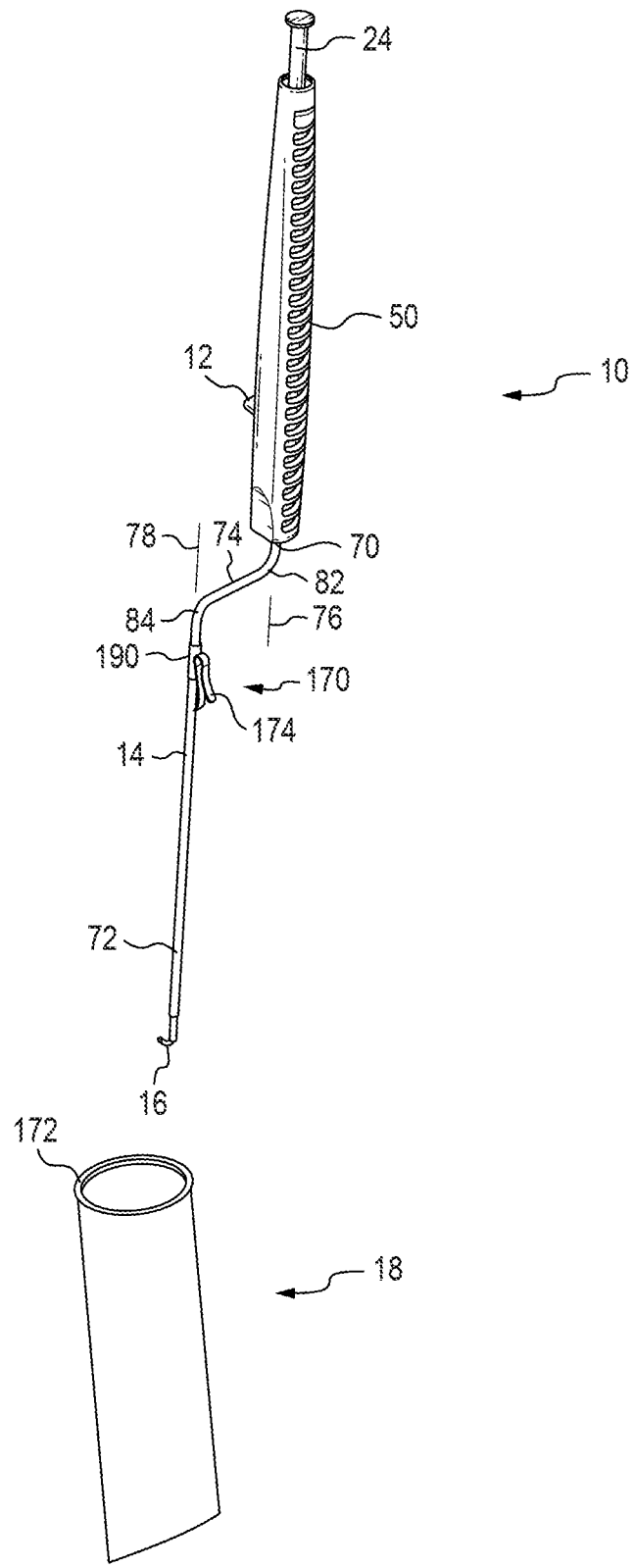
FIG. 2 is a perspective view of the suturing device of FIG. 1 prior to insertion into the tubular retractor.

The stabilizer 200 in FIGS. 5-7 includes a tubular retractor contact surface 230 extending away from the elongate body 14 configured to engage the upper edge 172 of the tubular retractor 18 (FIGS. 1 and 2). In this embodiment, the tubular retractor contact surface 230 is an inner surface on at least one of the inner leg 202 and the outer leg 204.

Figure 8:
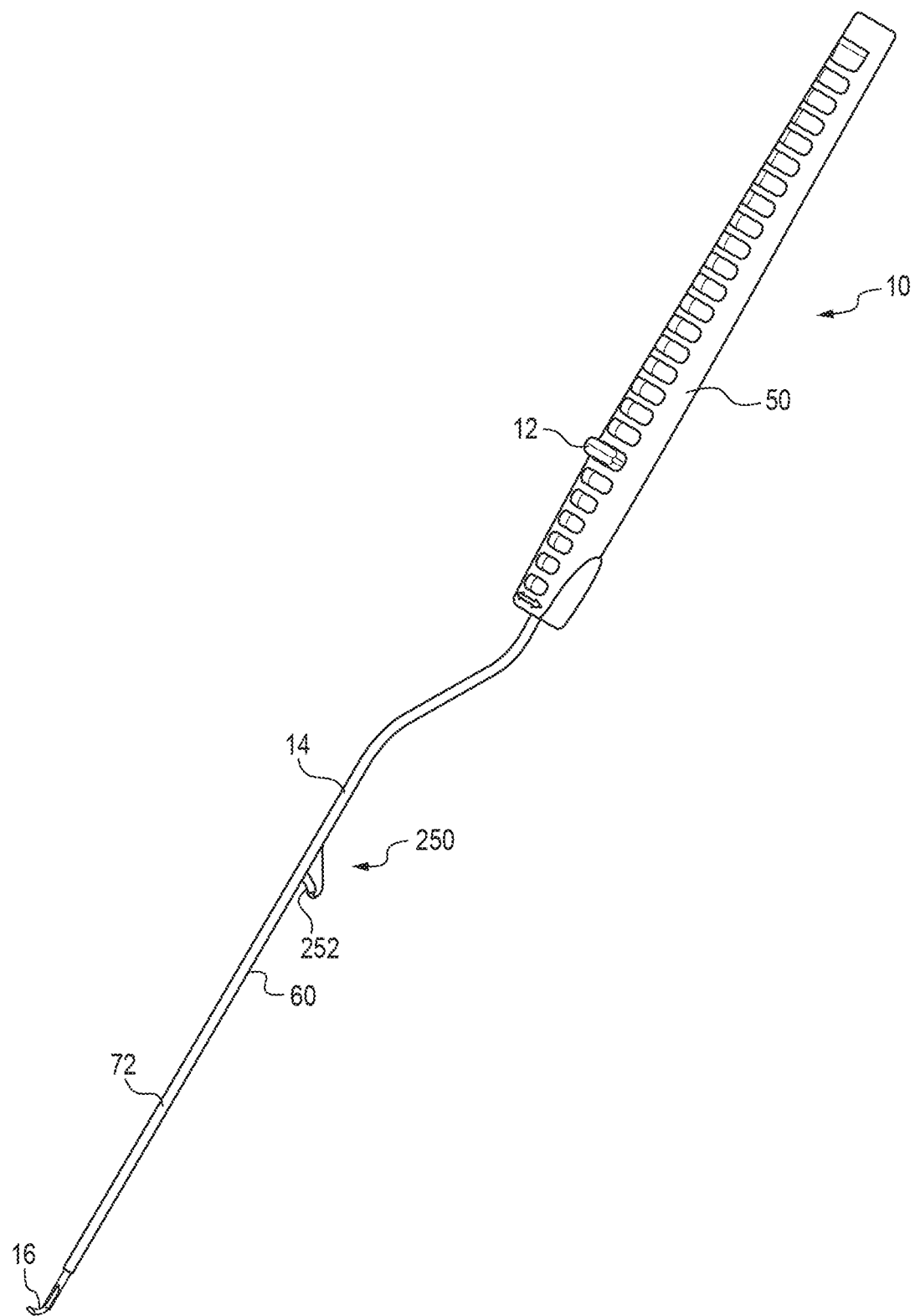
FIG. 8 is a perspective view of a suturing device having another alternative stabilizer

FIG. 8 depicts an alternative stabilizer 250 connected with the elongate body 14 and configured to engage the upper edge 172 (FIGS. 1 and 2) of the tubular retractor 18 so as to limit movement of the elongate body 14 with respect to the tubular retractor 18 when the stabilizer 250 is engaged with the tubular retractor 18. The stabilizer 250 includes a tubular retractor contact surface 252 extending away from the elongate body 14 configured to engage the upper edge 172 of the tubular retractor 18. The stabilizer 250 is generally triangular in shape when viewed from the side. The stabilizer 250 extends from the outer surface 60 of the elongate body 14 and is fixed to the elongate body 14 so that when the elongate body 14 is moved the stabilizer 250 is also moved. The tubular retractor contact surface 252 is a lower concave surface of the stabilizer 250 in the embodiment illustrated in FIG. 8.

In each embodiment, the stabilizer 170, 200 and 250 connects with the distal end portion 72 of the elongate body 14. The elongate body 14, however, could also take other configurations, e.g., straight, and the stabilizer 170, 200 and 250 could connect elsewhere. Each stabilizer 170, 200 and 250 can connect to the elongate body 14 such that the respective tubular retractor contact surface 184, 230 252 is offset at least 10 cm from the distal opening 146 (FIG. 3) measured in a direction parallel with a longitudinal axis (e.g., the distal end portion longitudinal axis 78) of the elongate body 14, which allows the needle holder 16 to be positioned below a lower end 260 of the tubular retractor 18 when the stabilizer 170, 200 and 250 is engaged with the upper edge 172 of the tubular retractor 18.

A suturing device has been described above with particularity. Modifications and alterations will occur to those upon reading and understanding the above detailed description. The invention, however, is not limited to only the embodiments described above. Instead, the invention is broadly defined by the appended claims and the equivalents thereof. Also, as used herein, the terms "comprises," "comprising," "includes," "including," "has," "having" or any other variation thereof, are intended to cover a non-exclusive inclusion. Also, various presently unforeseen or unanticipated alternatives, modifications, variations or improvements therein may be subsequently made by those skilled in the art which are also intended to be encompassed by the following claims.

The invention claimed is:

1. A suturing device comprising:
   an elongate body including a proximal end portion and a distal end portion;
   an actuator interacting with the elongate body and operable between a first operating position and a second operating position;
   a needle holder extending away from the distal end portion or provided as part of the distal end portion of the elongate body, the needle holder defining a needle passage and a distal opening;
   a spring clip connected with the elongate body and configured to engage an upper edge of an associated tubular retractor so as to limit movement of the elongate body with respect to the associated tubular retractor when the spring clip is engaged with the tubular retractor, wherein the spring clip includes a curved inner leg, a curved outer leg and a substantially upside-down U-shaped apex portion joining the curved inner leg to the curved outer leg.

2. The suturing device of claim 1, wherein the curved inner leg is spaced from the curved outer leg a minimum distance, which is less than or no more than 25% greater than a maximum wall thickness of an upper edge of a conventional 14-22 mm tubular retractor.

3. The suturing device of claim 2, wherein the spring clip configured to engage the upper edge of the associated tubular retractor is a first spring clip, and the stabilizer includes a second spring clip connected with the first spring clip and engaged with the elongate body.

4. The suturing device of claim 3, wherein the second spring clip connects with the elongate body and is slidable along the elongate body when connected with the elongate body.

5. A suturing device comprising:
an elongate body including a proximal end portion and a distal end portion;
an actuator interacting with the elongate body and operable between a first operating position and a second operating position;
a needle holder extending away from the distal end portion or provided as part of the distal end portion of the elongate body, the needle holder defining a needle passage and a distal opening;
a stabilizer connected with the elongate body and configured to engage an upper edge of an associated tubular retractor so as to limit movement of the elongate body with respect to the associated tubular retractor when the stabilizer is engaged with the tubular retractor, wherein the stabilizer includes a first spring clip configured to engage the upper edge of the associated tubular retractor, and a second spring clip connected with the first spring clip and engaged with the elongate body, wherein the second spring clip connects with the elongate body and is slidable along the elongate body when connected with the elongate body.

6. A suturing device comprising:
an elongate body including a proximal end portion and a distal end portion;
an actuator interacting with the elongate body and operable between a first operating position and a second operating position;
a needle holder extending away from the distal end portion or provided as part of the distal end portion of the elongate body, the needle holder defining a needle passage and a distal opening;
a stabilizer connected with the elongate body and configured to engage an upper edge of an associated tubular retractor so as to limit movement of the elongate body with respect to the associated tubular retractor when the stabilizer is engaged with the tubular retractor, wherein the stabilizer includes an inner leg configured to be received within the associated tubular retractor and an outer leg connected with the inner leg, wherein the outer leg is positioned outside of the tubular retractor when the stabilizer is engaged with the tubular retractor.

7. The suturing device of claim 6, wherein the outer leg is movable with respect to the inner leg.

8. The suturing device of claim 7, further comprising a trigger operatively connected with the outer leg.

9. The suturing device of claim 8, further comprising a handle connected with the elongate body, wherein the trigger is located adjacent to a distal end of the handle.

10. The suturing device of claim 9, wherein the trigger is spaced from the distal end of the handle in a distal direction.

11. The suturing device of claim 7, wherein the outer leg is biased toward the inner leg.

12. The suturing device of claim 11, further comprising a trigger operatively connected with the outer leg, wherein the trigger is configured to be movable from a first position toward a second position and movement from the first position toward the second position overcomes a biasing force biasing the outer leg toward the inner leg to move the outer leg with respect to the inner leg.

13. A suturing device comprising:
an elongate body including a proximal end portion and a distal end portion;
an actuator interacting with the elongate body and operable between a first operating position and a second operating position;
a needle holder extending away from the distal end portion or provided as part of the distal end portion of the elongate body, the needle holder defining a needle passage and a distal opening;
a curved needle received in the curved needle passage and having a first end, which is pointed, and a second end, wherein actuation of the actuator moves the curved needle in an advance direction;
a suture at least partially received in the curved needle passage and connected with the second end of the needle;
a stabilizer connected with the elongate body and configured to engage an upper edge of an associated tubular retractor so as to limit movement of the elongate body with respect to the associated tubular retractor when the stabilizer is engaged with the tubular retractor, wherein the stabilizer includes a tubular retractor contact surface extending away from the elongate body configured to engage the upper edge of the associated tubular retractor.

14. The suturing device of claim 13, wherein the stabilizer connects with the elongate body such that the tubular retractor contact surface is offset at least 10 cm from the distal opening measured in a direction parallel with a longitudinal axis of the elongate body.

* * * * *